United States Patent
Liu et al.

(10) Patent No.: US 11,857,838 B2
(45) Date of Patent: Jan. 2, 2024

(54) METHOD AND DEVICE FOR ASSESSING EXERCISE FATIGUE

(71) Applicant: Guangdong Coros Sports Technology Joint Stock Company, Dongguan (CN)

(72) Inventors: Xin Liu, Guangdong (CN); Xuan Rao, Guangdong (CN); Yu Tang, Guangdong (CN); Muyi Huang, Guangdong (CN); Haotian Niu, Guangdong (CN)

(73) Assignee: GUANGDONG COROS SPORTS TECHNOLOGY JOINT STOCK COMPANY, Guangdong (CN)

( * ) Notice: Subject to any disclaimer, the term of this patent is extended or adjusted under 35 U.S.C. 154(b) by 197 days.

(21) Appl. No.: 17/204,159

(22) Filed: Mar. 17, 2021

(65) Prior Publication Data
US 2021/0353999 A1 Nov. 18, 2021

(30) Foreign Application Priority Data
May 13, 2020 (CN) .......................... 202010401609.5

(51) Int. Cl.
*A63B 24/00* (2006.01)
*G16H 50/30* (2018.01)
(Continued)

(52) U.S. Cl.
CPC ...... *A63B 24/0062* (2013.01); *A61B 5/02438* (2013.01); *A61B 5/1112* (2013.01);
(Continued)

(58) Field of Classification Search
CPC ................ G16H 50/30; A63B 24/0062; A63B 2024/0065; A63B 2230/062;
(Continued)

(56) References Cited

U.S. PATENT DOCUMENTS

| 8,348,809 B2 * | 1/2013 | van der Zande .. A63B 24/0087 482/901 |
| 2006/0032315 A1 * | 2/2006 | Saalastic ................ A61B 5/222 73/808 |

(Continued)

FOREIGN PATENT DOCUMENTS

| CN | 107736886 A | 2/2018 |
| EP | 3391809 A | 10/2018 |

OTHER PUBLICATIONS

TrainingPeaks, 2016, https://web.archive.org/web/20161001043813/https://help.trainingpeaks.com/hc/en-us/articles/204071764-Form-TSB—(Year: 2016).*

*Primary Examiner* — Carl H Layno
*Assistant Examiner* — Michael J Lau
(74) *Attorney, Agent, or Firm* — Michael Best & Friedrich LLP

(57) ABSTRACT

A method for assessing exercise fatigue includes obtaining exercise heart rates of a user; calculating a CTL and an ATL based on the exercise heart rates and an exercise load computation model; calculating a TSB based on the CTL and the ATL; and determining a fatigue level based on the TSB. Such a determination of fatigue level will not be affected by subjective factors, thereby the scientificity and accuracy of the assessment result are effectively improved, and the assessment result is closer to the user's current physical function condition.

11 Claims, 2 Drawing Sheets

(51) Int. Cl.
*A61B 5/024* (2006.01)
*A61B 5/11* (2006.01)

(52) U.S. Cl.
CPC ............ *A61B 5/1118* (2013.01); *G16H 50/30* (2018.01); *A61B 2503/10* (2013.01); *A63B 2024/0065* (2013.01); *A63B 2220/62* (2013.01); *A63B 2230/062* (2013.01)

(58) Field of Classification Search
CPC . A61B 5/02438; A61B 5/1112; A61B 5/1118; A61B 2503/10
USPC ....................................................... 600/508
See application file for complete search history.

(56) References Cited

U.S. PATENT DOCUMENTS

| | | | |
|---|---|---|---|
| 2016/0263439 A1* | 9/2016 | Ackland | A61B 5/02405 |
| 2017/0258407 A1* | 9/2017 | Shirai | A61B 5/01 |
| 2017/0360368 A1* | 12/2017 | Aoshima | A61B 5/721 |
| 2019/0133495 A1* | 5/2019 | Mann | A61B 5/6898 |
| 2019/0214144 A1* | 7/2019 | Myllymäki | A61B 5/7275 |

* cited by examiner

METHOD AND DEVICE FOR ASSESSING EXERCISE FATIGUE

RELATED APPLICATIONS

This application claims the benefit of priority to Chinese invention applications No. 202010401609.5 filed on May 13, 2020, which is hereby incorporated by reference in its entirety.

FIELD OF THE INVENTION

The present invention relates to technical field of physical indicator assessment during a user's exercise, and in particular to a method and a device for assessing exercise fatigue.

BACKGROUND OF THE INVENTION

Exercise brings people health and happiness, without any doubt. However, excessive exercise may lead to over-fatigue, functional decline, sports injury, overtraining and other problems. Therefore, it's very important to scientifically and timely determine the fatigue degree so as to prevent excessive exercise and keep exercise in a safe and healthy range.

At present, the fatigue degree commonly is assessed by some subjective indicators such as self-feeling, complexion, perspiration, breathing, movement, and expert advice, which often fluctuate greatly due to weather conditions or other reasons, however. For example, running at the same pace, a user may feel comfortable if he/she is under a good condition and the weather is suitable, instead the user may feel tired if the weather is muggy and he/she had a bad sleep.

Nowadays, the fatigue degree may be assessed by using heart rate fluctuations of a user who wears a sports watch or a wristband with heart rate sensors embedded, to improve the objectivity in a certain extent. Nevertheless, it still cannot accurately reflect the user's physical condition, and the assessment result is unsatisfactory.

Therefore, it is necessary to improve the method for assessing exercise fatigue.

SUMMARY OF THE INVENTION

One objective of the present invention is to provide a method for assessing exercise fatigue, so as to objectively and accurately assess the fatigue degree of a user, as an effective exercise monitoring indicator in the current exercise.

Another objective of the present invention is to provide a device for assessing exercise fatigue, so as to objectively and accurately assess the fatigue degree of a user, as an effective exercise monitoring indicator in the current exercise.

To achieve the above objectives, the present invention provides a method for assessing exercise fatigue including:

obtaining exercise heart rates of a user;

calculating a chronic training load (CTL) and an acute training load (ATL) based on the exercise heart rates and an exercise load computation model;

calculating a training stress balance (TSB) based on the CTL and the ATL; and determining a fatigue level based on the TSB.

In comparison with the prior art, the method for assessing exercise fatigue according to the present invention firstly calculates the CTL and the ATL based on the exercise heart rates and a preset exercise load computation model, then calculate the TSB based on the CTL and the ATL, and finally determines a fatigue level based on the TSB. In such a way, the determination of the fatigue level in the present invention is based on the calculated objective data TSB, so that the determination will not be affected by subjective factors, thereby effectively improving the scientificity and accuracy of the assessment result. In addition, the TSB denotes the user's exercise load balance, which covers the impact of the user's long-term exercise load and short-term exercise load on the current exercise load that the user can withstand, so that the determined fatigue level according to the present method is closer to the user's current physical function condition.

Preferably, the TSB is obtained by calculating a difference between the CTL and the ATL.

Preferably, if a value of the TSB is with an interval [0.1CTL, +∞], the fatigue level is determined to be energetic;

if a value of the TSB is within an interval [−0.4CTL, 0.1CTL), the fatigue level is determined to be appropriate;

if a value of the TSB is within an interval [−0.7CTL, −0.4CTL), the fatigue level is determined to be greater;

if a value of the TSB is within an interval [−∞, −0.7CTL), the fatigue level is determined to be excessive.

Preferably, the exercise load computation model is: $TR=\Sigma_1^T B*C*T_K$, wherein TR denotes an exercise load, T denotes the user's continuous exercise time for each time, B=(exercise heart rate−resting heart rate)/(maximum heart rate−resting heart rate), $C=P1*e^{P2*B}$, P1 is a constant between 0.1 and 0.5, P2 is a constant between 2.5 and 7, and $T_K$ is a temperature influence coefficient obtained by querying a temperature influence coefficient table recording multiple influence coefficients of different temperatures on exercise load; the resting heart rate is a heart rate value of the user under awake and quiet state; and the maximum heart rate is a heart rate value of the user when the user reaches an extreme exercise state.

Preferably, the exercise load computation model further includes an altitude parameter, and the exercise load computation model is: $TR=\Sigma_1^T B*C*TK*GK$, wherein $G_K$ is an altitude influence coefficient obtained by querying an altitude influence coefficient table recording multiple influence coefficients of different altitudes on the exercise load.

Preferably, the exercise load computation model further includes an exercise item parameter, and the exercise load computation model is: $TR=\Sigma_1^T B*C*T_K*G_K*X_K$, wherein $X_K$ is an exercise item influence coefficient obtained by querying an exercise item influence coefficient table recording multiple influence coefficients of different exercise items on the exercise load.

Accordingly, the present invention further provides a device for assessing exercise fatigue including:

a heart rate sensor configured to obtain exercise heart rates of a user;

a computation module configured to calculate a chronic training load (CTL) and an acute training load (ATL) based on the exercise heart rates and an exercise load computation model, and calculate a training stress balance (TSB) based on the CTL and the ATL; and a matching module configured to determine a fatigue level based on the TSB.

Preferably, the TSB is obtained by calculating a difference between the CTL and the ATL.

Preferably, if a value of the TSB is with an interval [0.1CTL, +∞], the fatigue level is determined to be energetic;

if a value of the TSB is within an interval [−0.4CTL, 0.1CTL), the fatigue level is determined to be appropriate:

if a value of the TSB is within an interval [−0.7CTL, −0.4CTL), the fatigue level is determined to be greater;

if a value of the TSB is within an interval [−∞, −0.7CTL), the fatigue level is determined to be excessive.

Preferably, the exercise load computation model is: $TR=\Sigma_1^T B*C*TK$, wherein TR denotes an exercise load, T denotes the user's continuous exercise time for each time, B=(exercise heart rate−resting heart rate)/(maximum heart rate−resting heart rate), $C=P1*e^{P2*B}$, P1 is a constant between 0.1 and 0.5, P2 is a constant between 2.5 and 7, and $T_K$ is a temperature influence coefficient obtained by querying a temperature influence coefficient table recording multiple influence coefficients of different temperatures on exercise load; the resting heart rate is a heart rate value of the user under awake and quiet state; and the maximum heart rate is a heart rate value of the user when the user reaches an extreme exercise state.

Preferably, the exercise load computation model further includes an altitude parameter, and the exercise load computation model is: $TR=\Sigma_1^T B*C*TK*GK$, wherein $G_K$ is an altitude influence coefficient obtained by querying an altitude influence coefficient table recording multiple influence coefficients of different altitudes on the exercise load.

Preferably, the exercise load computation model further includes an exercise item parameter, and the exercise load computation model is: $TR=\Sigma_1^T B*C*T_K*G_K*X_K$, wherein $X_K$ is an exercise item influence coefficient obtained by querying an exercise item influence coefficient table recording multiple influence coefficients of different exercise items on the exercise load.

The present invention also provides a computer readable storage medium including computer programs configured to be executed by a processor to implement the method for assessing exercise fatigue as described above.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

In order to explain in detail the technical content, construction features, the purpose and effect achieved by the present invention, the following combined with the implementation and the attached drawings are described in detail.

Figure 1:
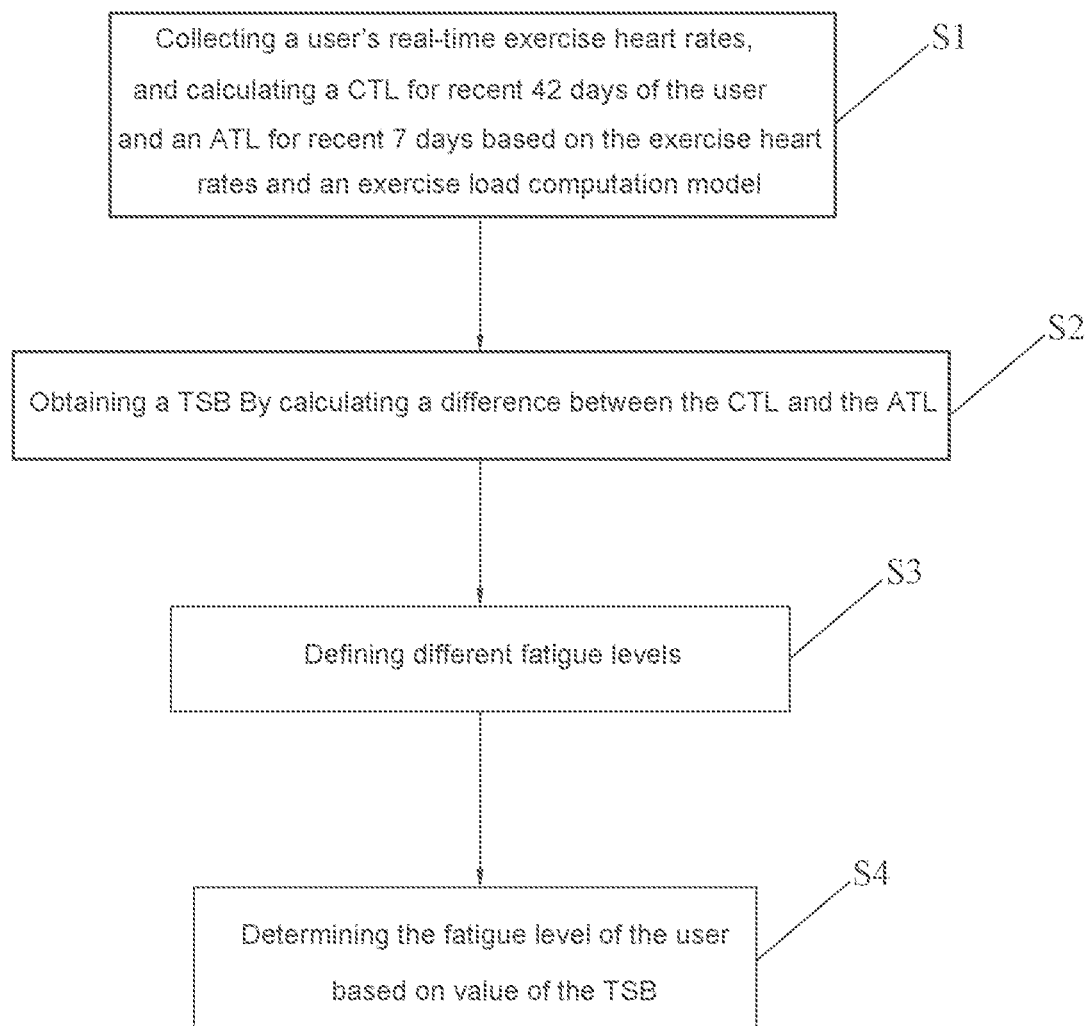
FIG. 1 is a schematic diagram of the flowchart of a method for assessing exercise fatigue according to an embodiment of the present invention.

Referring to FIG. 1, the present invention provides a method for assessing exercise fatigue, and the method include the following steps:

S1, collecting a user's real-time exercise heart rates, and calculating a chronic training load (CTL) for recent N days of the user and an acute training load (ATL) for recent M days based on the exercise heart rates and an exercise load computation model. Preferably, N is much greater than M; more preferably, the value of N is 42, and the value of M is 7, for example. If the currently recorded exercise time is less than 42 days or 7 days, an average of the exercise load of the longest exercise time currently recorded is calculated.

S2, obtaining a training stress balance (TSB) by calculating a difference between the CTL and the ATL, namely, TSB=CTL−ATL. In such a way, the exercise load that the user's current body functions can bear may be accurately assessed.

S3, defining different fatigue levels, including Level A, Level B, Level C, . . . and so on, for example. In this embodiment, the fatigue levels may be energetic, appropriate, greater, and excessive.

S4, based on value of the TSB, determining the fatigue level of the user. That is, the larger the value of the TSB is, the higher the fatigue level is (namely, the better the current physical condition is, and the lower the fatigue degree is); instead, the smaller value of the TSB is, the lower the fatigue level is (namely, the worse the current physical condition is, the higher the fatigue degree is).

As known, a user's physical function is affected by the intensity of long-term exercise, the intensity of long-term exercise is greater, the exercise intensity that can be withstood during the current exercise will be greater. Therefore, the user's physical function condition can be characterized by the TSB that is the difference between the CTL and the ATL. The fatigue level is determined based on the 'T'SB in the above embodiment, so that the determined fatigue level is closer to the user's current physical function condition. In addition, in the calculation process of the TSB, the CTL and the ATL are obtained through a preset exercise load computation model based on o real-time exercise heart rate Therefore, TSB is a completely objective parameter, so that the determination of the fatigue level is not affected by subjective factors, thereby effectively improving the objectivity and accuracy of exercise fatigue assessment.

In a preferable embodiment, multiple intervals are divided with using CTL as the standard parameter.

Specifically, if the value of the TSB is with the interval [0.1CTL, +∞], the fatigue level is determined to be energetic; if the value of the TSB is within the interval [−0.4CTL, 0.1CTL), the fatigue level is determined to be appropriate; if the value of the TSB is within the interval [−0.7CTL, −0.4CTL), the fatigue level is determined to be greater; and if the value of the TSB is within the interval [−∞, −0.7CTL), the fatigue level is determined to be excessive.

In the present invention, the exercise load computation model may apply a common exercise load computation model or other models. Preferably, the exercise load computation model is $TR=\Sigma_1^T B*C*T_K$, wherein TR denotes an exercise load. T denotes the user's continuous exercise time for each time, B=(exercise heart rate−resting heart rate)/ (maximum heart rate−resting heart rate), $C=P1*e^{P2*B}$, P1 is a constant between 0.1 and 0.5, P2 is a constant between 2.5 and 7, and $T_K$ is a temperature influence coefficient obtained by querying a temperature influence coefficient table (as shown in Table 1) recording multiple influence coefficients of different temperatures on exercise load.

TABLE 1

| Temperature (° C.) | Temperature influence coefficient |
|---|---|
| 25 | 1 |
| 26 | 1.1 |
| 27 | 1.2 |
| 28 | 1.3 |
| 29 | 1.4 |

TABLE 1-continued

| Temperature (° C.) | Temperature influence coefficient |
|---|---|
| 30 | 1.5 |
| 31 | 1.6 |
| 32 | 1.7 |
| 33 | 1.8 |
| 34 | 1.9 |

The resting heart rate is the heart rate value of a user under awake and quiet state, and the maximum heart rate is the heart rate value of a user when the user reaches an extreme exercise state.

The resting heart rate and the maximum heart rate can be detected by a portable detecting device or preset by the user manually when the resting heart rate and the maximum heart rate are known to the user, alternatively can be calculated based on the user's age through the formula $HR_{max}=208-0.7*a$, wherein $HR_{max}$ denotes the maximum heart rate, and a is the age input by the user.

If the current continuous exercise time is one hour (3600 seconds), the exercise load in this one hour is $\Sigma_1^{3600} B*C*T_K$, that is because the exercise heart rate is collected once per second.

Furthermore, the exercise load is also affected by altitude. A user may consume more exercise loads in high altitude areas. In view of it, the exercise load computation model further includes an altitude parameter, namely the exercise load computation model is $TR=\Sigma_1^T B*C*T_K*G_K$, wherein $G_K$ is an altitude influence coefficient obtained by querying an altitude influence coefficient table (as shown in Table 2) recording multiple influence coefficients of different altitudes on the exercise load.

TABLE 2

| Altitude (m) | Altitude influence coefficient |
|---|---|
| below 1500 | 1 |
| 1600 | 1.1 |
| 1700 | 1.2 |
| 1800 | 1.3 |
| 1900 | 1.4 |
| 2000 | 1.5 |
| 2100 | 1.6 |
| 2200 | 1.7 |
| 2300 | 1.8 |
| 2400 | 1.9 |

Additionally, the exercise load may be also affected by different exercise items, in a preferable embodiment, the exercise load computation model further includes an exercise item parameter, namely the exercise load computation model is: $TR=\Sigma_1^T B*C*T_K*G_K*X_K$, where $X_K$ is an exercise item influence coefficient obtained by querying an exercise item influence coefficient table (as shown in Table 3) recording multiple influence coefficients of different exercise items on the exercise load.

TABLE 3

| Exercise item | Exercise item influence coefficient |
|---|---|
| Running | 1 |
| Riding | 0.6 |
| Swimming | 1.5 |
| Boxing | 3.5 |

In conclusion, the method for assessing exercise fatigue according to the present invention collects the exercise heart rates of the user, the current temperature, attitude and exercise item, then obtains a temperature influence coefficient $T_K$, an altitude influence coefficient $G_K$, and an exercise item influence coefficient $X_K$ by querying the corresponding data table, then calculates the user's exercise load during the exercise time period through the exercise load computation model $TR=\Sigma_1^T B*C*T_K*G_K*X_K$ based on the resting heart rate, maximum heart rate, exercise heart rate, coefficients $T_K$, $G_K$, and $X_K$; and then cumulative exercise loads for each day are saved in units of days; then, CTL for the recent 42 days and ATL for the recent 7 days are calculated by using moving average algorithm, and a TSB is obtained by calculating a difference between the average CTL and the average ATL; finally a fatigue level is determined by judging which interval the current TSB is located.

Figure 2:
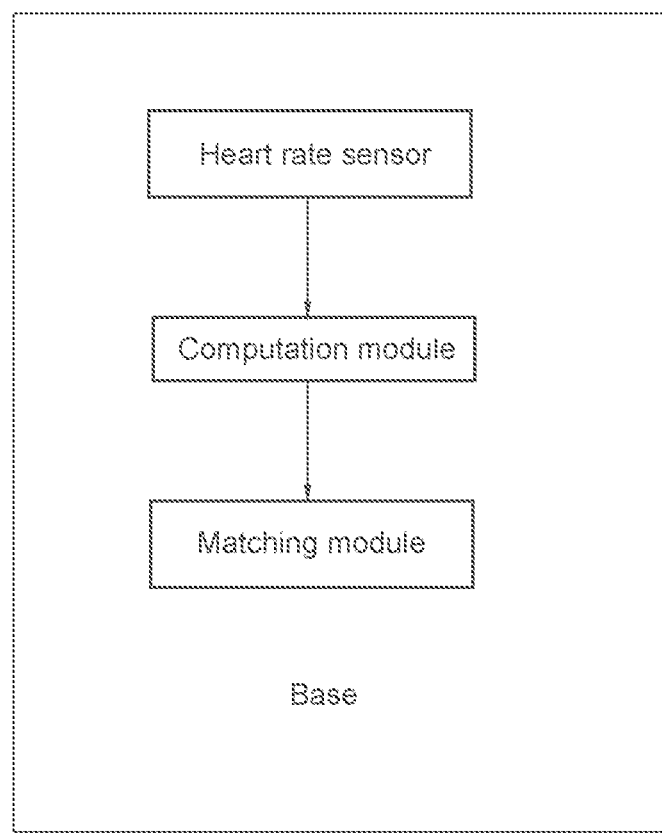
FIG. 2 is a schematic diagram of a device for assessing exercise fatigue according to an embodiment of the present invention.

Accordingly, the present invention further provides a device for assessing exercise fatigue, as shown in FIG. 2. The device includes a portable base (such as a sports watch or a wristband) on which a heart rate sensor, a computation module and a matching module are configured.

Specifically, the heart rate sensor is configured to collect a user's real-time exercise heart rates.

The computation module is configured to calculate a CTL for recent N days and an ATL for recent M (N is much greater than M, preferably) days based on the exercise heart rates and a preset exercise load computation model, and obtain a TSB by calculating a difference between the CTL and the ATL, namely, TSB=CTL−ATL.

The matching module is configured to determine a fatigue level based on the TSB. Different fatigue levels represent different fatigue degrees.

The working principle and detailed working process of the device for assessing exercise fatigue in this embodiment will not be repeated here, please refer to the above method for assessing exercise fatigue for details.

While the invention has been described in connection with what are presently considered to be the most practical and preferred embodiments, it is to be understood that the invention is not to be limited to the disclosed embodiments, but on the contrary, is intended to cover various modifications and equivalent arrangement included within the spirit and scope of the invention.

What is claimed is:

1. A computer-implemented method for assessing exercise fatigue, wherein the method uses a computer to perform steps comprising:

obtaining exercise heart rates, a resting heart rate and a maximum heart rate of a user;

establishing an exercise load computation model based on the exercise heart rates, the resting heart rate and the maximum heart rate;

calculating a chronic training load (CTL) and an acute training load (ATL) based on the exercise heart rates and the exercise load computation model;

calculating a training stress balance (TSB) based on the CTL and the ATL; and determining a fatigue level based on the TSB;

wherein the exercise load computation model is: $TR=\Sigma_1^T B*C*T_K$, wherein TR denotes an exercise load, T denotes the user's continuous exercise time for each time, B=(exercise heart rate−resting heart rate)/(maximum heart rate−resting heart rate), $C=P1*e^{P2*B}$, P1 is a constant between 0.1 and 0.5, P2 is a constant between 2.5 and 7, and $T_K$ is a temperature influence coefficient obtained by querying a temperature influence coefficient table recording multiple influence coefficients of different temperatures om exercise load;

the resting heart rate is a heart rate value of the user when the user reaches an extreme exercise state.

2. The computer-implemented method for assessing exercise fatigue as claimed in claim 1, wherein the TSB is obtained by calculating a difference between the CTL and the ATL.

3. The computer-implemented method for assessing exercise fatigue as claimed in claim 2, wherein
if a value of the TSB is with an interval [0.1CTL, +ω], the fatigue level is determined to be energetic;
if a value of the TSB is within an interval [−0.4CTL, 0.1CTL), the fatigue level is determined to be appropriate;
if a value of the TSB is within an interval [−0.7CTL, −0.4CTL), the fatigue level is determined to be greater;
if a value of the TSB is within an interval [−ω, −0.7CTL), the fatigue level is determined to be excessive.

4. The computer-implemented method for assessing exercise fatigue as claimed in claim 1, wherein the exercise load computation model further includes an altitude parameter, and the exercise load computation model is: $TR=\Sigma_1^T B*C*T_K*G_K$, wherein $G_K$ is an altitude influence coefficient obtained by querying an altitude influence coefficient table recording multiple influence coefficients of different altitudes on the exercise load.

5. The computer-implemented method for assessing exercise fatigue as claimed in claim 4, wherein the exercise load computation model further includes an exercise item parameter, and the exercise load computation model is: $TR=\Sigma_1^T B*C*T_K*G_K*X_K$, wherein $X_K$ is an exercise item influence coefficient obtained by querying an exercise item influence coefficient table recording multiple influence coefficients of different exercise items on the exercise load.

6. A computer readable storage medium, comprising computer programs configured to be executed by a processor to implement the computer implemented method for assessing exercise fatigue according to claim 1.

7. A device for assessing exercise fatigue, comprising:
a heart rate sensor configured to obtain exercise heart rates, a resting heart rate and a maximum heart rate of a user;
an exercise load computation model based on the exercise heart rates, the resting heart rate and the maximum heart rate;
a computation module configured to calculate a chronic training load (CTL) and an acute training load (ATL) based on the exercise heart rates and the exercise load computation model, and calculate a training stress balance (TSB) based on the CTL and the ATL; and
a matching module configured to determine a fatigue level based on the TSB;
wherein the exercise load computation model is: $TR=\Sigma_1^T B*C*T_K$, wherein TR denotes an exercise load, T denotes the user's continuous exercise time for each time, B=(exercise heart rate−resting heart rate)/(maximum heart rate−resting heart rate), $C=P1*e^{P2*B}$, P1 is a constant between 0.1 and 0.5, P2 is a constant between 2.5 and 7, and $T_K$ is a temperature influence coefficient obtained by querying a temperature influence coefficient table recording multiple influence coefficients of different temperatures om exercise load; the resting heart rate is a heart rate value of the user when the user reaches an extreme exercise state.

8. The device for assessing exercise fatigue as claimed in claim 7, wherein the TSB is obtained by calculating a difference between the CTL and the ATL.

9. The device for assessing exercise fatigue as claimed in claim 8, wherein
if a value of the TSB is with an interval [0.1CTL, +ω], the fatigue level is determined to be energetic;
if a value of the TSB is within an interval [−0.4CTL, 0.1CTL), the fatigue level is determined to be appropriate;
if a value of the TSB is within an interval [−0.7CTL, −0.4CTL), the fatigue level is determined to be greater;
if a value of the TSB is within an interval [−ω, −0.7CTL), the fatigue level is determined to be excessive.

10. The device for assessing exercise fatigue as claimed in claim 7, wherein the exercise load computation model further includes an altitude parameter, and the exercise load computation model is: $TR=\Sigma_1^T B*C*T_K*G_K$, wherein $G_K$ is an altitude influence coefficient obtained by querying an altitude influence coefficient table recording multiple influence coefficients of different altitudes on the exercise load.

11. The device for assessing exercise fatigue as claimed in claim 10, wherein the exercise load computation model further includes an exercise item parameter, and the exercise load computation model is: $TR=\Sigma_1^T B*C*T_K*G_K*X_K$, $X_K$ is an exercise item influence coefficient obtained by querying an exercise item influence coefficient table recording multiple influence coefficients of different exercise items on the exercise load.

* * * * *